United States Patent [19]

Crevier et al.

[11] Patent Number: 4,496,090

[45] Date of Patent: Jan. 29, 1985

[54] SURGICAL STAPLER

[76] Inventors: Paul H. Crevier, 436 Melbourne Ave., Mount Royal, Quebec, Canada, H3P 1H2; Istvan Lindmayer, 4390 Gilles St., Pierrefonds, Quebec, Canada, H9H 2N4

[21] Appl. No.: 356,813

[22] Filed: Mar. 10, 1982

[51] Int. Cl.$^3$ .............................................. A61B 17/04
[52] U.S. Cl. ........................................ 227/19; 227/83; 227/DIG. 1
[58] Field of Search ....................... 227/DIG. 1, 19, 83

[56] References Cited

U.S. PATENT DOCUMENTS

| | | | |
|---|---|---|---|
| 2,237,438 | 4/1941 | James | 227/83 |
| 2,440,479 | 4/1948 | Lang | 227/83 |
| 3,120,230 | 2/1964 | Skold | 227/DIG. 1 |
| 3,339,265 | 9/1967 | Powers et al. | 227/83 X |
| 3,915,366 | 10/1975 | Mitchell | 227/83 |
| 4,169,476 | 10/1979 | Hiltebrandt | 227/DIG. 1 |
| 4,246,903 | 1/1981 | Larkin | 227/DIG. 1 |
| 4,304,236 | 12/1981 | Conta et al. | 227/DIG. 1 |
| 4,402,444 | 9/1983 | Green | 227/19 |

Primary Examiner—Paul A. Bell
Attorney, Agent, or Firm—Emory L. Groff, Jr.

[57] ABSTRACT

A stapler for interconnecting adjacent penetrable bodies such as vertebrae includes a barrel with a staple support and deforming anvil at one end thereof; a plunger slidably mounted in the barrel for pressing the staple against the anvil to deform and drive the staple out of the stapler into the vertebrae; a handle and trigger at the other end of the handle for driving the plunger against the anvil and out of the stapler; a helical spring for returning the plunger to the rest position; and a control sleeve and pin arrangement for placing the plunger in the "DISMANTLE", "LOAD", "SAFE" or "FIRE" position, in which the stapler can be dismantled or assembled, loaded, inserted into position or fired.

2 Claims, 25 Drawing Figures

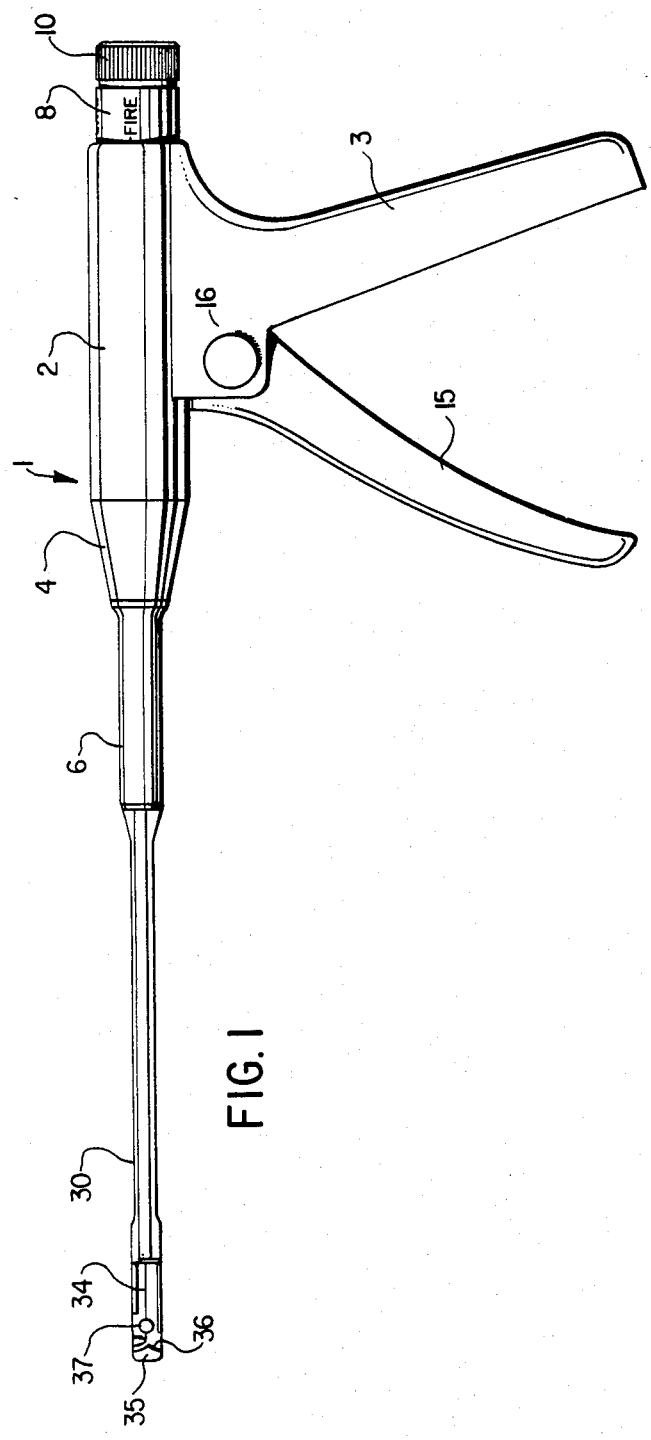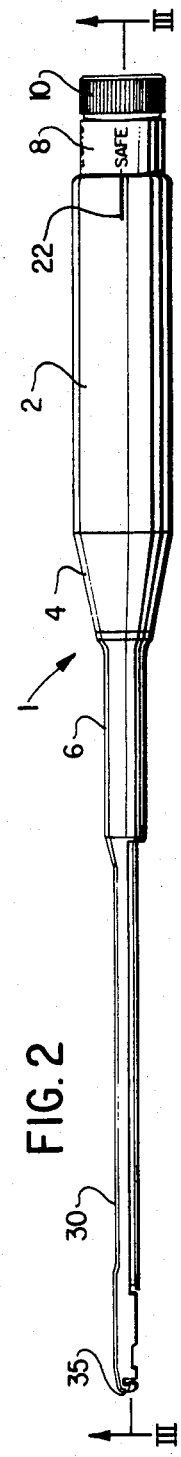
FIG.1
FIG.2

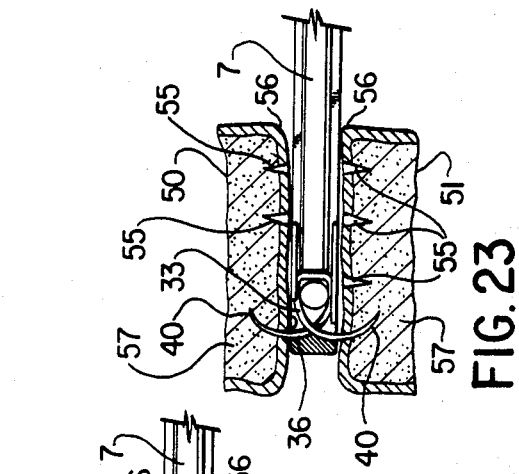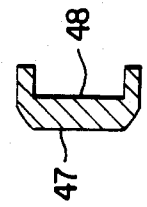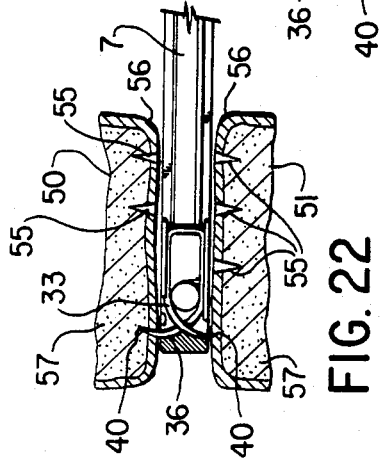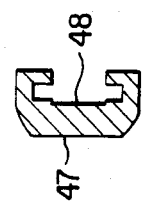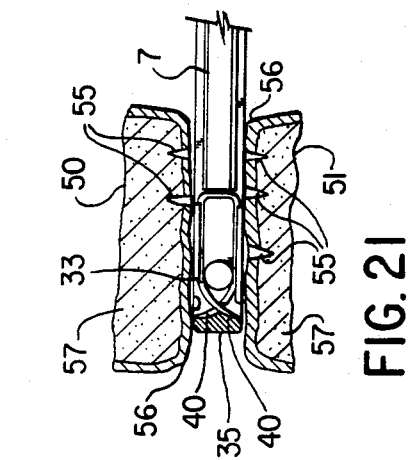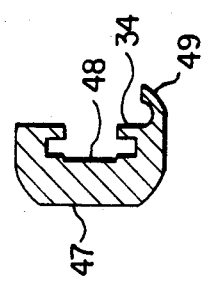

SURGICAL STAPLER

BACKGROUND OF THE INVENTION

1. Field of the Invention

This invention relates to a stapler, and in particular to a surgical stapler which is primarily intended for use in the interconnecting of spinal vertebrae.

While the thrust of the following is toward the use of the stapler for interconnecting adjacent vertebrae, it will be appreciated that the stapler can be used in a similar manner to interconnect any adjacent penetrable elements.

2. Discussion of the Prior Art

Back problems and more specifically problems involving the discs located between the vertebrae are responsible for much pain and suffering. When a disc is ruptured or otherwise damaged, one solution to the problem has been to remove the disc. At present, the resulting space is often left empty, causing instability and pain due to arthritis. In some cases, the resulting space has been filled with bone blocks, or dowels, taken from another area of the patient's body or from a cadaver, or filled with a prosthesis of the type disclosed for example by Canadian Pat. No. 992,235, issued to Cutter Laboratories, Inc. on July 6, 1976, and U.S. Pat. No. 3,875,595, issued to E. C. Froning on April 8, 1975. The insertion of a plastic cushion between the two vertebrae bodies is unlikely to correct the instability, since such a foreign body will probably be dislodged.

Bone grafting, either between the bodies or along the posterior arches of vertebrae has met with limited success. Because there is a difference in hardness between the graft bone and the vertebrae which causes wear, even if cancellous surfaces have been carefully opposed, the union between the graft bone and the vertebrae often fails. Stalactities and stalagmites grow out of the grafted bone irritating roots in the area. Patients often complain that they have the impression that the disc has been replaced with a cement block.

Thus, it is readily apparent that there exists a need for an alternative method of interconnecting the vertebrae following disc removal. There is also a need for a device for performing such an operation. The object of the present invention is to provide a stapler, which can be used to interconnect adjacent articles such as vertebrae.

GENERAL DESCRIPTION OF THE INVENTION

Accordingly, the present invention relates to a stapler for inserting a staple into at least one of a pair of articles to facilitate interconnection of the articles comprising:

(a) a casing, said casing including
  (i) handle means at one end thereof for manual operation of the stapler,
  (ii) an elongated barrel integral with said handle defining the other end of said casing,
  (iii) support means at the free end of said barrel remote from said handle for supporting a deformable staple, and
  (iv) anvil means at said free end of said barrel for deforming the staple;
(b) plunger means slidably mounted in said barrel for bearing against the staple to deform the latter and force a pointed end of the staple out of the barrel in a direction perpendicular to the longitudinal axis thereof into said article;
(c) trigger means at said one end of said casing for moving said plunger means from a rest position to a staple ejecting position; and
(d) spring means in said casing for returning said plunger means to the rest position.

The invention also provides a surgical method, in which the disc between adjacent vertebrae of the spine is removed; the cartilage is scraped from the vertebral surfaces; if necessary, the intervertebral space is enlarged; a plurality of staples are inserted into the vertebrae; and the remaining space is backfilled with a plastic or decalcified bone powder. The plastic or bone powder seals the staples in position so that they do not travel to another area of the body such as the spinal cord or nervous structures therearound, or to the peritoneal cavity,

BRIEF DESCRIPTION OF DRAWINGS

The invention will now be described in greater detail with reference to the accompanying drawings, which illustrate preferred embodiments of the invention, and wherein:

FIG. 1 is a side elevation view of one embodiment of stapler in accordance with the present invention;

FIG. 2 is a plan view of the stapler of FIG. 1;

Figures 16, 17:
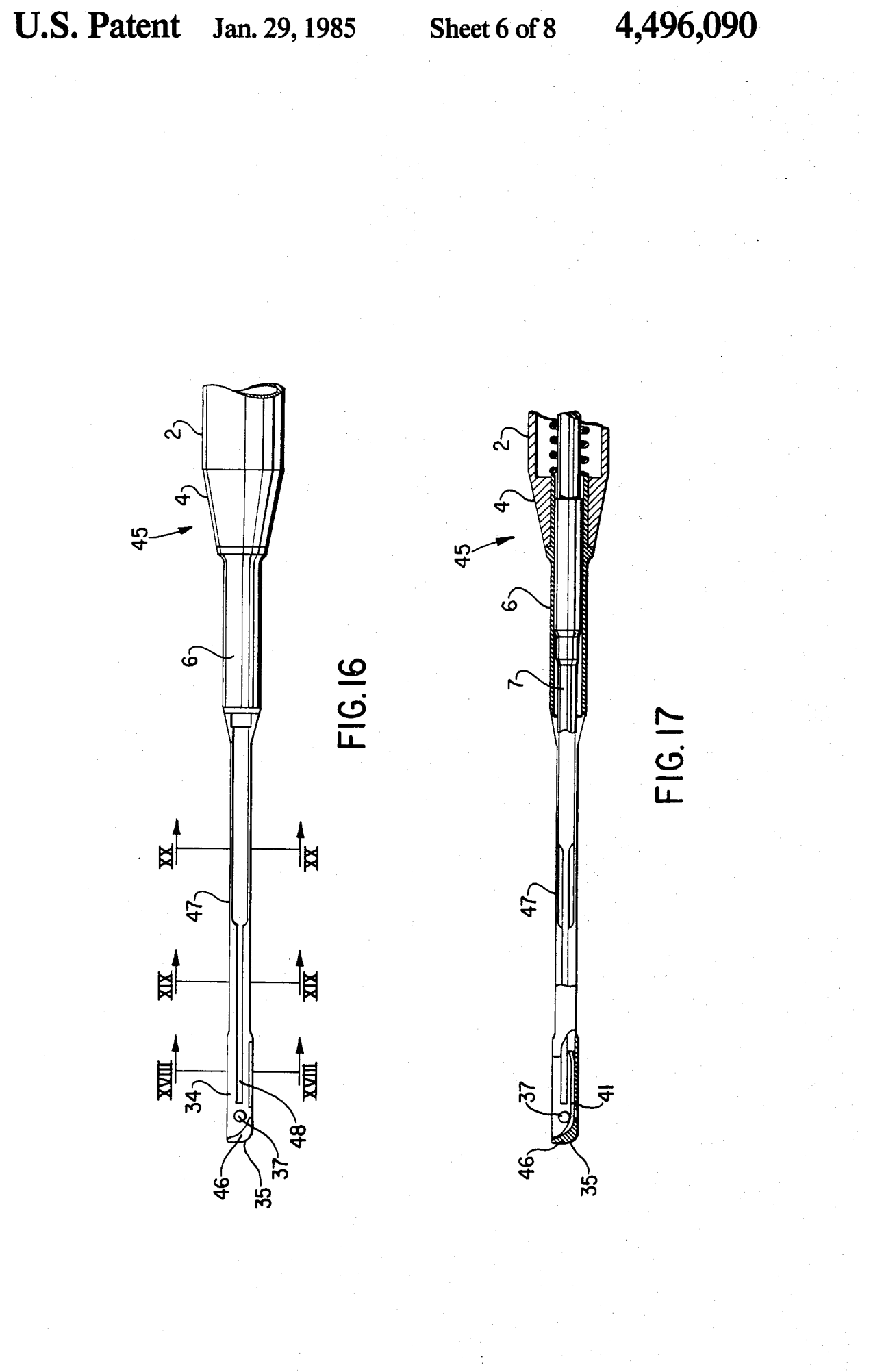

FIG. 16 is a side elevation of one end of the second embodiment of the stapler;

FIG. 17 is a longitudinal sectional view of the stapler of FIG. 16;

FIGS. 18 to 20 are cross-sections taken generally along lines XVIII—XVIII, XIX—XIX and XX—XX, respectively of FIG. 16;

FIGS. 21 to 23 are cross-sectional views of portions of adjacent vertebrae showing the use of the stapler of FIGS. 1 to 9;

DESCRIPTION OF PREFERRED EMBODIMENTS

Figure 3:
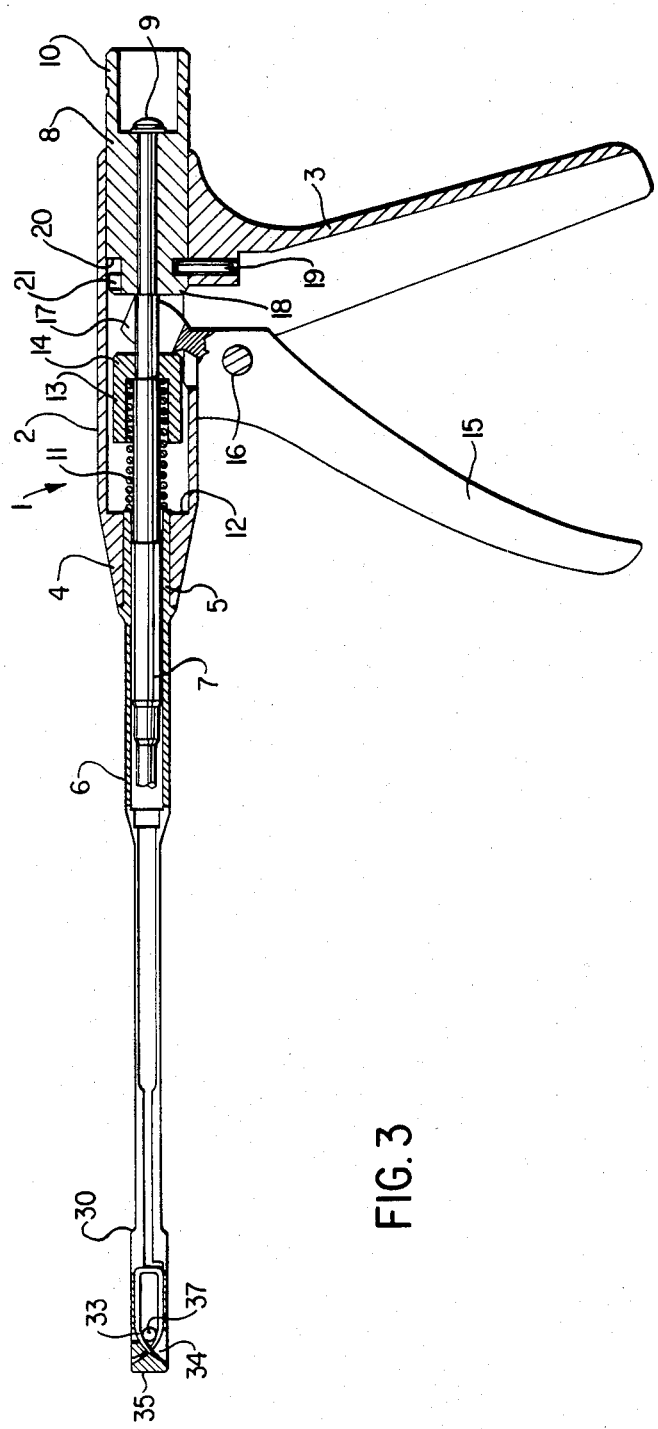
FIG. 3 is a cross-section taken generally along line III—III of FIG. 2 with parts removed.
Figure 4:
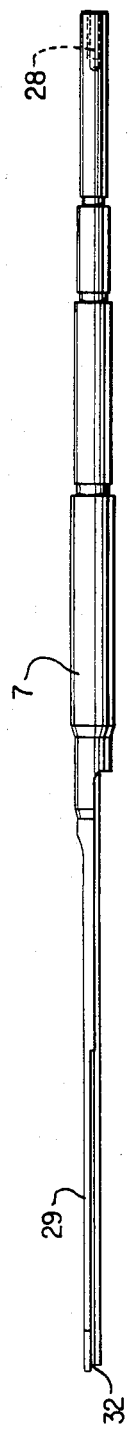
FIG. 4 is a plan view of a plunger used in the apparatus of FIGS. 1 to 3.
Figure 5:
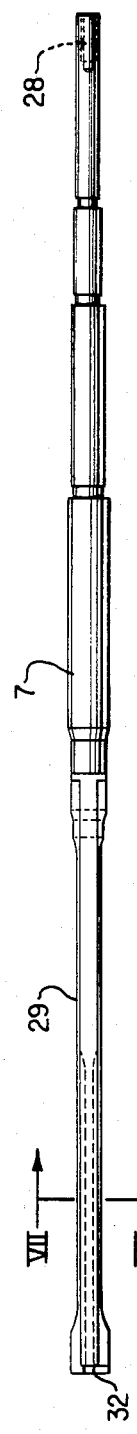
FIG. 5 is a side elevation view of the plunger of FIG. 4.
Figure 7:
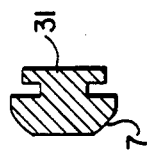
FIG. 7 is a cross-section taken generally along line VII—VII of FIG. 5.
Figure 6:
FIG. 6 is an end view of the plunger of FIGS. 4 and 5, from the left of FIG. 5.

With reference to FIGS. 1 to 3 of the drawings, one embodiment of the stapler of the present invention includes a casing generally indicated at 1. One end portion 2 of the casing 1 is tubular with a handle 3 extending outwardly from one side thereof. The handle 3 has a generally U-shaped cross-sectional configuration, and is integral with the casing 1. End 4 of the portion 3 is tapered for receiving one end 5 of a smaller diameter portion 6. The two portions 2 and 6 of the casing define an elongated barrel for slidably supporting a plunger 7 (FIGS. 4 to 7). A control sleeve 8 is rotatably mounted on one end of the plunger 7. A screw 9 in recessed end 10 of the sleeve 8 holds the sleeve on the plunger 7. Longitudinally extending grooves are provided in the outer surface of the end 10 of the sleeve 8, facilitating manual gripping of the control sleeve. The plunger 7 and the sleeve 8 are biased to the rest position (FIGS. 1 to 3) by a helical spring 11. The spring 11 is mounted on the plunger 7 and extends between an internal shoulder 12 near the tapered end of the portion 2 of the casing 1 and a sleeve 13, which is fixedly mounted on the plunger 7 in front of the control sleeve 8. The sleeve 13 includes a rear flange 14, radially inwardly extending for retaining the spring 11.

A trigger 15 is pivotally connected to the casing 1 immediately in front of the handle 3 for rotation around a screw 16. The end of the trigger 15 within the casing 1 is bifurcated, the two arms thereof defining lugs 17 (one shown) which lie on either side of the plunger 7 within a gap between the front end of the sleeve 8 and the rear end of the sleeve 13. When the trigger 15 is squeezed towards the handle 3, the lugs 17 press against the rear end of the sleeve 13 to move the plunger 7 forwardly compressing the spring 11.

Figure 9:
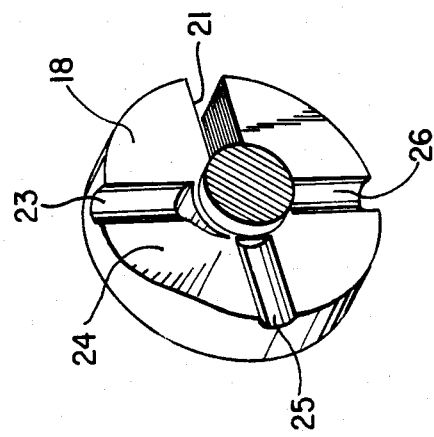
FIG. 9 is a perspective view of a portion of the control sleeve of FIG. 8.
Figure 8:
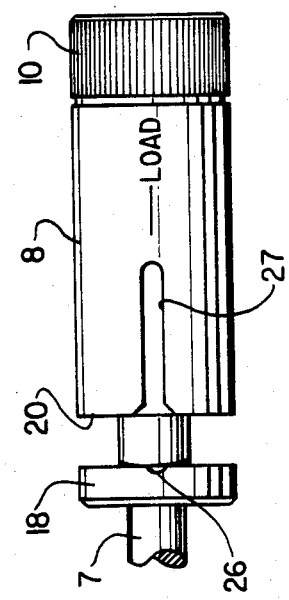
FIG. 8 is a plan view of the handle end of a control sleeve of the stapler of FIGS. 1 to 3.
Figure 10:
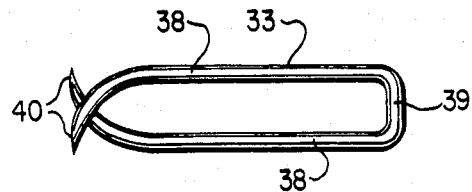
FIG. 10 is a plan view of a staple used in the stapler of FIGS. 1 to 9.
Figure 11:
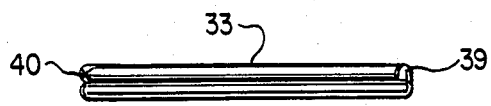
FIG. 11 is a side elevation view of the staple of FIG. 10.
Figure 12:
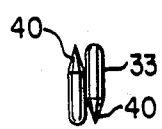
FIGS. 12 and 13 are end views of the staple of FIGS. 10 and 11.
Figure 13:
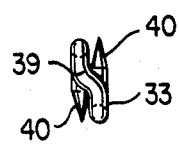

Referring to FIGS. 3, 8 and 9, movement of the plunger 7 and of the sleeves 8 and 13 is controlled by an annular flange 18 on the front end of the control sleeve 8, and a pin 19 fixedly mounted in the top end of the handle 3 and normally extending into an annular groove 20 between the flange 18 and the main body of the sleeve 8. There are four positions of the sleeve 8 in the casing 1, namely the "DISMANTLE", "LOAD", "SAFE" and "FIRE" positions.

In the "DISMANTLE" position of the sleeve 8, the pin 19 is aligned with a slot 21 in the flange 18, so that the pin can pass freely through the flange 18, Thus in the "DISMANTLE" position of the sleeve 8, when the screw 16 and handle 15 are removed, the plunger 7 and sleeves 8 and 13 can be removed from or inserted into the casing to dismantle or assemble the stapler. In the "DISMANTLE" position, the slot 21 is at the bottom of the casing in alignment with the pin 19, and the abbreviation "DISM" appears on the top of the control sleeve 8 in alignment with an indicator line 22 (FIG. 2) on the top of the rear portion 2 of the casing 1.

In the "LOAD" position of the stapler, limited longitudinal movement of the plunger 7 is required. For such purpose, a relatively deep, concave, axially extending groove 23 is provided in the rear surface of the flange 18. The sleeve 8 is biased rearwardly by the spring 11 so that the pin 19 seats in the groove 23, but limited forward and rearward movement of the plunger 7 is possible. In the "LOAD" position, the word "LOAD" appears on the top of the control sleeve 8 in longitudinal alignment with the indicator line 22. One side of the groove 23 is cut away, so a flat cam surface 24 follows the groove 23 in the direction toward the "SAFE" position. Thus, it is easier to rotate the sleeve 8 from the "LOAD" to the "SAFE" position than from the "LOAD" to the "DISMANTLE" position.

In the "SAFE" position, the pin 19 sits in a shallow, concave, radially extending groove 25 so that the plunger 7 cannot be moved forwardly against a staple. In such "SAFE" position, the shallow concave groove 25 is at the bottom of the casing 1 and the word "SAFE" appears on the top of the sleeve 8 in alignment with the indicator line 22. The provision of a "SAFE" position of the control sleeve 8 prevents the discharging of a staple until the barrel is properly positioned.

Finally, the control sleeve 8 is rotated to the "FIRE" position in which the pin 19 rests in a shallow concave groove 26 in the flange 18 until pressure is applied to the trigger 15. When the trigger 15 is squeezed, the lugs 17 push the plunger 7 forwardly with the sleeves 8 and 13. The pin 19 slides freely in a longitudinally extending groove 27 in the body of the sleeve 8 opposite the groove 26 (FIG. 8). The plunger 7 can be moved forwardly a distance sufficient to discharge a staple.

Referring again to FIGS. 1, 3 and 4, the plunger 7 is defined by an elongated rod with a threaded hole 28 for receiving the screw 9. The end 29 of the plunger 7 remote from the handle 3 is exposed, i.e. one side of the leading end 30 of the casing 1 is cut away, so that movement of the plunger 7 can be observed. One side 31 of the leading end 29 of the plunger 7 is generally T-shaped (FIGS. 4 to 7) for sliding in a T-shaped slot (not shown) in leading end 30 of the casing 1. The outer or front end of the plunger 7 is flared slightly and cut away to define a shoulder 32, which bears against a staple 33 (FIGS. 3, and 10 to 13) when the latter is placed on a support surface 34 at the front end of the casing 1.

The leading edge 35 of the casing 1 includes a shoulder 36, which defines a generally V-shaped anvil for deforming the staple 33 in conjunction with a post 37.

Figure 24:
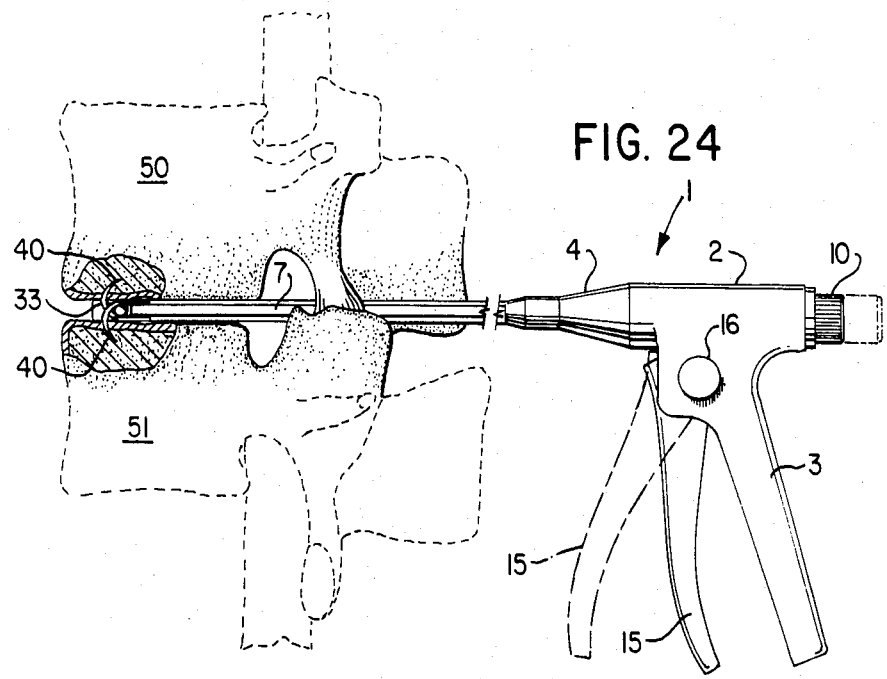
FIG. 24 is a partly sectioned, side elevation view of adjacent vertebrae and the stapler of FIGS. 1 to 9.
Figure 25:
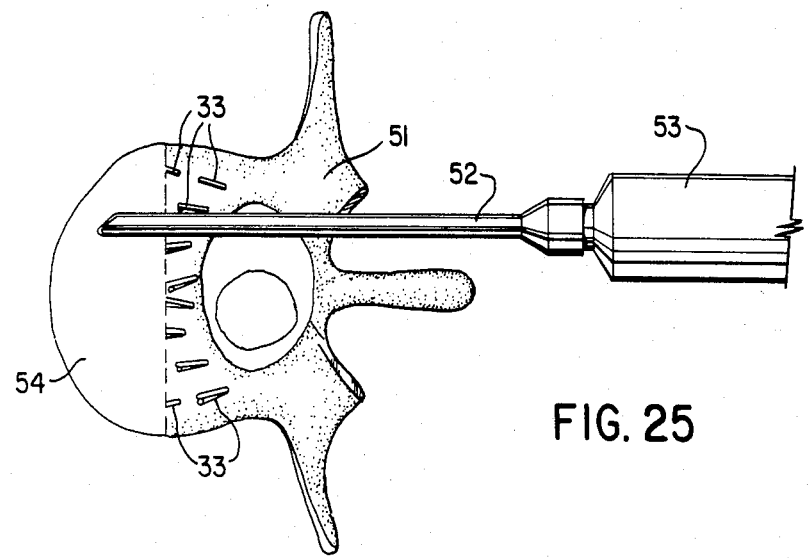
FIG. 25 is a plan view of a single vertebrae and one end of a syringe for inserting plastic between the adjacent vertebrae.

As best seen in FIGS. 3 and 10 to 13, the staple 33 includes a generally U-shaped body defined by a pair of straight arms 38 interconnected by a bight 39. The arms 38 lie in separate planes, and their pointed free ends 40 overlap, i.e. the pointed free ends 40 of the arms 39 curve inwardly into overlapping relationship with each other. Thus, when the plunger 7 is forced forwardly, the arms 38 of the staple 33 are deformed by the anvil 36 to define a tight loop (FIGS. 23 and 24).

Figure 14:
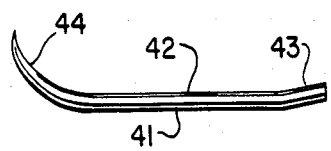
FIG. 14 is a plan view of a staple for use in a second embodiment of the stapler of the present invention.
Figure 15:
FIG. 15 is an end view of the staple of FIG. 14.

Referring now to FIGS. 14 and 15, an alternative form of staple 41 for use with the second embodiment of the present invention is defined by a straight body 42 with a slightly curved rear end 43 and a markedly curved, pointed front end 44.

The staple 41 is used with a stapler, the front end of which is generally indicated at 45 (FIGS. 16 and 17) which is virtually identical to the stapler of FIGS. 1 to 9. Accordingly, wherever possible the reference numerals of FIGS. 1 to 9 have been used in FIGS. 16 and 17. In the second embodiment of the stapler, the front end 35 of the casing 1 includes an anvil 46 designed to deform the staple 41, so that the latter bends around the pin 37 and is discharged perpendicular to the longitudinal axis of the plunger 7 and casing 1. The front end 47 of the casing 1 has a cross-section similar to that of the leading or front end 30 of the first embodiment, i.e. the front end 47 includes a channel 48 in which the plunger 7 can slide. The channel is rectangular at the rear end and T-shaped at the front end. The plunger 7 is similarly shaped for firm engagement with the casing 1. A side wall and staple guide 49 is provided on one side of the front end 47 of the casing 1 for retaining the body 42 of the staple 41 and guiding the latter against the anvil 46.

When the first embodiment of the stapler of the present invention is being used to prepare a spinal prosthesis (FIGS. 21 to 25), the first step is to completely remove the disc (not shown) from betweeen adjacent vertebrae 50 and 51. The cartilage is scraped from the vertebrae surfaces and, if necessary, the intervertebral space is enlarged using a standard vertebral spreader. With the stapler in "LOAD" position, a stainless steel staple 33 is placed on the support surface 34 in the stapler. The control sleeve 8 is rotated to the "SAFE" position, so that the staple 33 cannot be accidentally ejected, and the front end 35 of the stapler is inserted between the vertebrae 50 and 51. When the stapler is in the desired position, the sleeve 8 is rotated to the "FIRE" position and the trigger 15 is squeezed, moving from the phantom outline position of FIG. 24 to the solid outline position of the same figure. As best shown in FIGS. 21 to 23 the squeezing of the trigger 15 causes forward movement of the plunger 7. During such forward plunger movement the ends 40 of the staple 33 are deformed outwardly from the stapler by the anvil 36 entering the vertebrae 50 and 51. Upon completion of a staple insertion operation, the end 35 of the casing 1 is moved slightly to disengage the anvil 36 and the pin 37 from the staple 33. A plurality of staples 33 are inserted into the vertebrae. Then, nozzle 52 of a syringe 53 is placed between the vertebrae 50 and 51 to backfill such space with plastic 54 such as an acrylic plastic or with decalcified bone powder. When decalcified bone powder is used, perforations 55 are formed through cortical bone 56 into cancellous bone 57, so that blood flows from the cancellous bone into the bone powder to promote the formation of osseous cells therein. The perforations 55 are made prior to staple insertion, preferably using an instrument similar to the stapler of the present invention. For example, the plunger could include an extension on the front end thereof for extension into the bone and retraction therefrom.

When using the staples 41 with the second embodiment of the stapler, a plurality of such staples 41 are inserted into both vertebrae 50 and 51 so that curved outer ends thereof extend toward without touching the other vertebrae. The plastic 53 or decalcified bone powder is inserted between the vertebrae to stabilize the staples and lock the vertebrae 50 and 51 together.

While the use of the staplers has been described in connection with the production of a vertebral prothesis, it will be appreciated that the first embodiment of the stapler could be used alone to interconnect other adjacent bodies which are penetrable by the staples. Moreover, either form of stapler could be used with a plastic to interconnect articles other than vertebrae.

It is readily apparent that in the foregoing expressions such as "front end" and "leading end" are used in connection with the discharge end of the stapler, "rear end" and "trailing end" are used in connection with the handle/trigger end, and "top" refers to the area of the stapler uppermost when the stapler is picked up by the user.

We claim:

1. A stapler for inserting a staple into a pair of adjacent articles to facilitate interconnection of the articles comprising a casing including handle means thereof for manual operation of the stapler, an elongated barrel integral with said handle means defining the other end of said casing, support means at the free end of said barrel remote from said handle means for supporting a deformable staple, and fixed, substantially V-shaped anvil means at said free end of said barrel for forcing overlapping pointed free ends of a substantially U-shaped staple out of the barrel in opposite directions perpendicular to the longitudinal axis of said barrel into both said articles; plunger means slidably mounted in said barrel for bearing against the staple to deform the latter and force the pointed ends of the staple out of the barrel into said articles; trigger means at said one end of said casing for moving said plunger means from a rest position to a staple ejecting position; spring means in said casing for returning said plunger means to the rest position; control sleeve means rotatably mounted on said one end of said plunger means and projecting out of said casing for controlling movement of said plunger means in said barrel; and pin means in said casing for engaging said control sleeve means to permit or prevent movement of said plunger means in said barrel; said control sleeve means including an annular flange and an annular groove on the inner end thereof, said groove slidably receiving said pin means, a slot in said flange permitting passage of said pin means through said flange for assembling and dismantling of the stapler, the remainder of said flange preventing movement of said plunger against the staple, and a longitudinally extending channel in said sleeve connected to and perpendicular to said groove permitting longitudinal movement of said plunger against a staple.

2. A stapler according to claim 1, including lever means pivotally connected to said handle means for movement toward said handle means; and lug means on one end of said lever means in said barrel for engaging said plunger means and moving the plunger means against the staple.

* * * * *